(12) United States Patent
Jack et al.

(10) Patent No.: US 10,473,548 B2
(45) Date of Patent: Nov. 12, 2019

(54) METHOD AND APPARATUS FOR DETECTING PRESENCE OF A FLUID

(71) Applicant: GM Global Technology Operations LLC, Detroit, MI (US)

(72) Inventors: Philip S. Jack, Waren, MI (US); Douglas R. Drauch, Troy, MI (US); John M. Thornton, Rochester Hills, MI (US); Philip Wolschendorf, Rochester Hills, MI (US); Joshua L. Engle, Birmingham, MI (US); Derek M. Arrotta, Ferndale, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 183 days.

(21) Appl. No.: 15/688,392

(22) Filed: Aug. 28, 2017

(65) Prior Publication Data

US 2019/0063973 A1    Feb. 28, 2019

(51) Int. Cl.
*G01M 3/16* (2006.01)
*H01M 10/42* (2006.01)
*G01N 33/28* (2006.01)

(52) U.S. Cl.
CPC .............. *G01M 3/16* (2013.01); *G01N 33/28* (2013.01); *H01M 10/4228* (2013.01)

(58) Field of Classification Search
CPC .......... G01M 3/16; G01M 3/40; G01M 3/186; H01M 10/4228; G01N 27/12
See application file for complete search history.

(56) References Cited

U.S. PATENT DOCUMENTS

| 5,070,300 | A | * | 12/1991 | Matsui | ............... G01N 15/1031 324/464 |
| 7,927,505 | B2 | * | 4/2011 | Kormann | ................. C09K 5/10 252/74 |
| 9,465,000 | B1 | * | 10/2016 | Brown | ................. G01N 27/026 |
| 2018/0080891 | A1 | * | 3/2018 | Potyrailo | ............... G01N 27/04 |

* cited by examiner

*Primary Examiner* — Justin N Olamit
(74) *Attorney, Agent, or Firm* — Quinn IP Law

(57) ABSTRACT

A device for detecting presence of a fluid is described, and includes a resistive sensing element including a first conductive element proximal to a second conductive element, wherein the first conductive element is electrically isolated from the second conductive element, and a controller disposed to monitor electrical conductivity between the first conductive element and the second conductive element. The controller includes an instruction set that is executable to periodically monitor a signal associated with the electrical conductivity between the first conductive element and the second conductive element. A baseline value for the electrical conductivity between the first conductive element and the second conductive element can be determined based upon the periodically monitored signal, and a signal waveform can be determined based upon the periodically monitored signal. The signal waveform can be characterized, and presence of a fluid can be detected based upon the characterized waveform.

15 Claims, 2 Drawing Sheets

METHOD AND APPARATUS FOR DETECTING PRESENCE OF A FLUID

INTRODUCTION

Presence of fluids near an electrical device such as an inverter or high-voltage battery can negatively affect service life thereof.

SUMMARY

A device for detecting presence of a fluid is described, and includes a resistive sensing element including a first conductive element proximal to a second conductive element, wherein the first conductive element is electrically isolated from the second conductive element, and a controller disposed to monitor electrical conductivity between the first conductive element and the second conductive element. The controller includes an instruction set that is executable to periodically monitor a signal associated with the electrical conductivity between the first conductive element and the second conductive element. A baseline value for the electrical conductivity between the first conductive element and the second conductive element is determined based upon the periodically monitored signal, and a signal waveform is determined based upon the periodically monitored signal. The signal waveform is characterized, and presence of a fluid is detected based upon the characterized waveform.

An aspect of the disclosure includes the instruction set being executable to detect presence of standing water at the resistive sensing element when the signal waveform (signature) is characterized as a step response.

Another aspect of the disclosure includes the instruction set being executable to detect presence of condensate water at the resistive sensing element when the signal waveform is characterized as a negative decayed response.

Another aspect of the disclosure includes the instruction set being executable to detect presence of coolant at the resistive sensing element when the signal waveform is characterized as an initial step response followed by a positive decayed response.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which.

It should be understood that the appended drawings are not necessarily to scale, and present a somewhat simplified representation of various preferred features of the present disclosure as disclosed herein, including, for example, specific dimensions, orientations, locations, and shapes. Details associated with such features will be determined in part by the particular intended application and use environment.

DETAILED DESCRIPTION

The components of the disclosed embodiments, as described and illustrated herein, may be arranged and designed in a variety of different configurations. Thus, the following detailed description is not intended to limit the scope of the disclosure, as claimed, but is merely representative of possible embodiments thereof. In addition, while numerous specific details are set forth in the following description in order to provide a thorough understanding of the embodiments disclosed herein, some embodiments can be practiced without some of these details. Moreover, for the purpose of clarity, certain technical material that is understood in the related art has not been described in detail in order to avoid obscuring the disclosure. Furthermore, the drawings are in simplified form and are not to precise scale. Furthermore, the disclosure, as illustrated and described herein, may be practiced in the absence of an element that is not specifically disclosed herein.

Figure 1:
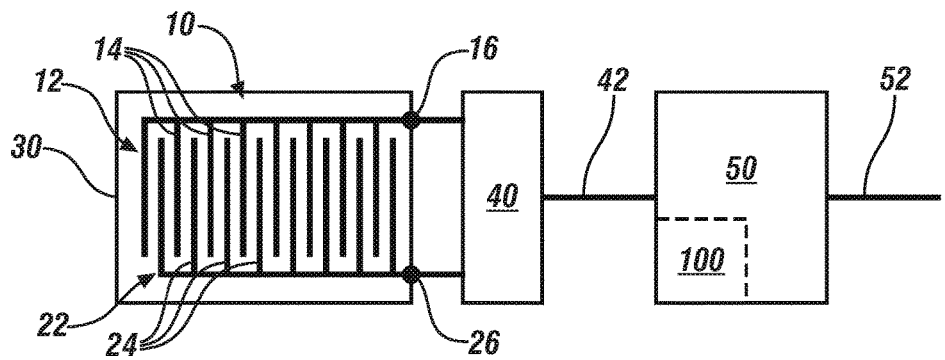
FIG. 1 schematically illustrates a device for detecting presence of a fluid, including a resistive sensing element and an associated signal conditioning circuit that is in communication with a controller, in accordance with the disclosure FIG. 2 schematically shows a control routine for monitoring and evaluating a signal output from the signal conditioning circuit coupled to the resistive sensing element, in accordance with the disclosure.

Referring to the drawings, wherein like reference numerals correspond to like or similar components throughout the several Figures, FIG. 1, consistent with embodiments disclosed herein, schematically illustrates a device for detecting presence of a fluid, including a resistive sensing element 10 and an associated signal conditioning circuit 40 that is in communication with a controller 50. The resistive sensing element 10 can be advantageously disposed proximal to an electrical device such as an inverter or high-voltage battery on a vehicle to monitor for and detect presence of fluids such as coolant or water. The presence of coolant or water can be the result of a leak in a coolant circuit, for example. The presence of fluids can negatively affect service life of the inverter or high-voltage battery.

The resistive sensing element 10 includes a first electrode 12 and a second electrode 22 that are disposed on a substrate 30. The first electrode 12 includes a plurality of first legs 14, and the second electrode 22 includes a plurality of second legs 24. The first and second electrodes 12, 22 are disposed on the substrate 30 such that the first legs 14 alternate with and proximal to the second legs 24. The first and second electrodes 12, 22 including the first and second legs 14, 24 are shown as being arranged in a rectilinear configuration, but may be another configuration, including, e.g., curved shapes, S-shapes, etc. The first electrode 12 includes a first terminal 16, and the second electrode 22 includes a second terminal 26, wherein the first and second terminals 16, 26 can electrically connect to or otherwise communicate with the controller 50. The first electrode 12 including the first legs 14 are electrically isolated from the second electrode 22 including the second legs 24. As such, the electrical resistance between the first electrode 12 and the second electrode 22 is theoretically infinite, and is practically greater than 10 Megohms absent the presence of a foreign material such as coolant or water that electrically bridges therebetween.

The first and second electrodes 12, 22 including the first and second legs 14, 24 can be fabricated from conductive material that can include conductive metals, metal oxides, carbon-based materials, organic materials and polymer materials. The substrate 30 is formed from a non-conductive material that can be rigid or flexible. The first and second electrodes 12, 22 can be assembled onto the substrate 30 employing adhesive material, or etching into the surface of the substrate 30 when the substrate 30 is a semi-conductor wafer, or employing another mechanism.

The signal conditioning circuit 40 is in communication with the first and second electrodes 12, 22 via electrically conductive leads or another mechanism. The signal conditioning circuit 40 includes a DC power source, resistive devices, operational amplifiers and/or other electrical elements that supply electrical power to the first and second electrodes 12, 22 and monitor electrical resistance thereacross. The signal conditioning circuit 40 is in communication with the controller 50, and communicates a signal that is input to the controller 50 via a communication link 42. In one embodiment, the signal output from the signal conditioning circuit 40 that is communicated via the communication link 42 to the controller 50 is an analog signal that correlates to the electrical resistance or conductivity across the first and second electrodes 12, 22. The signal conditioning circuit 40 can be incorporated into the controller 50 in one embodiment.

The controller 50 includes a control routine 100 that monitors the signal output from the signal conditioning circuit 40 that is communicated via the communication link 42, and generates a communication output 52 in response. The term "controller" and related terms such as control module, module, control, control unit, processor and similar terms refer to one or various combinations of Application Specific Integrated Circuit(s) (ASIC), electronic circuit(s), central processing unit(s) that include microprocessor(s) and associated non-transitory memory component(s) in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean controller-executable instruction sets including calibrations and look-up tables. The controller executes control routine(s) to provide desired functions. Routines may be executed at regular intervals, for example each 100 microseconds during ongoing operation. Alternatively, routines may be executed in response to occurrence of a triggering event. Communication between controllers, and communication between controllers, actuators and/or sensors may be accomplished using a direct wired point-to-point link, a networked communication bus link, a wireless link or another suitable communication link. Communication includes exchanging data signals in suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to a physically discernible indicator that conveys information, and may be a suitable waveform (e.g., electrical, optical, magnetic, mechanical or electromagnetic), such as DC, AC, sinusoidal-wave, triangular-wave, square-wave, vibration, and the like, that is capable of traveling through a medium.

Figure 2:
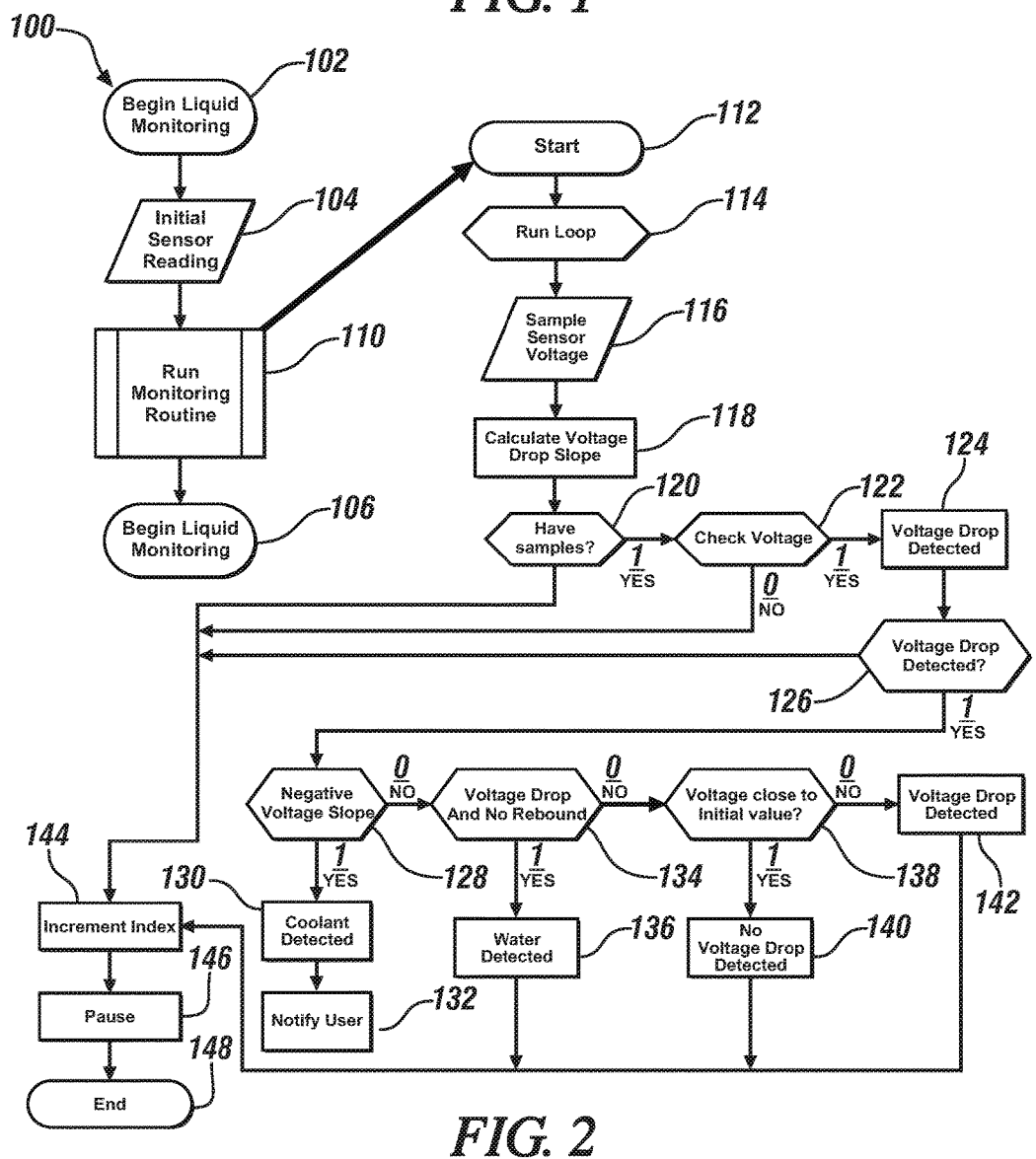

FIG. 2 schematically shows details of the control routine 100 that executes to monitor and evaluate the signal output from the signal conditioning circuit 40, and generates a signal output 52 in response. The signal output 52 from the control routine 100 indicates presence or absence of a fluid on the sensor 10, and further discriminates the signal output 52 to discern the substance of the fluid that is present at the sensor 10. In this embodiment, the signal output 52 discerns whether the fluid present at the sensor 10 is water in liquid form, i.e., freestanding water, water in condensate form, i.e., moisture, or coolant. When the device is deployed in an automotive environment, the coolant can be a solution of an organic chemical and water, wherein the organic chemical is composed of ethylene glycol, diethylene glycol, propylene glycol, and the like.

Table 1 is provided as a key wherein the numerically labeled blocks and the corresponding functions are set forth as follows, corresponding to the routine 100. The teachings may be described herein in terms of functional and/or logical block components and/or various processing steps. It should be realized that such block components may be composed of hardware, software, and/or firmware components that have been configured to perform the specified functions.

TABLE 1

| BLOCK | BLOCK CONTENTS |
|-------|----------------|
| 102 | Begin Monitoring |
| 104 | Take initial sensor reading |
| 110 | Run monitoring routine |
| 112 | Start |
| 114 | Run continuous loop |
| 116 | Sample sensor output signal (voltage) |
| 118 | Calculate voltage drop slope |
| 120 | Sample size large enough? |
| 122 | Check voltage slope |
| 124 | Voltage drop is detected |
| 126 | Is voltage drop detected? |
| 128 | Is there a voltage drop with rebound? |
| 130 | Coolant detected |
| 132 | Notify operator |
| 134 | Is there a voltage drop without rebound? |
| 136 | Water detected |
| 138 | Did voltage level return to initial value? |
| 140 | No voltage drop detected |
| 142 | Condensation detected |
| 144 | Increment index |
| 146 | Pause |
| 148 | End |

Execution of the routine 100 may proceed as follows. The steps of the process 100 may be executed in a suitable order, and are not limited to the order described with reference to FIG. 2.

The monitoring can commence at any time (102), and may commence in conjunction with a vehicle key-on event when the routine 100 is executed on a vehicle. An initial sensor reading is captured (104), and is employed as a baseline sensor value. The baseline sensor value is a measure of electrical resistance or conductivity across the first and second electrodes 12, 22, and is theoretically infinite or greater than a predetermined value, which is greater than 10 Megohms in one embodiment. In one embodiment, the baseline sensor value may instead be a pre-calibrated value that is stored in a memory device. The monitoring routine 110 begins execution after the baseline sensor value has been captured. The monitoring routine 110 includes an initiation step (112) and a loop step (114) to permit periodic execution. The monitoring routine 110 then commences to periodically monitor a signal output from the sensor 10 via the signal conditioning circuit 40 and the communication link 42 (116) and characterizes the signal waveform, including calculating a voltage drop slope based thereon (118). A sample counter is interrogated to determine whether a sufficient sample size has been reached (120), and if so (120)(1), the signal waveform and the voltage drop slopes are evaluated (122), (124) and (126) to determine if a voltage drop has been detected. When no voltage drop has been detected (126)(0), the iteration ends by incrementing the sample counter (144) and pauses for a period of time, e.g., 0.1 seconds (146) before initiating the next iteration of the routine (114). When a voltage drop has been detected (126)(1), the signal waveforms including the voltage drop slopes are evaluated (steps 128, 134, 138, 142) to determine what is indicated by the signal waveform.

Figure 3:
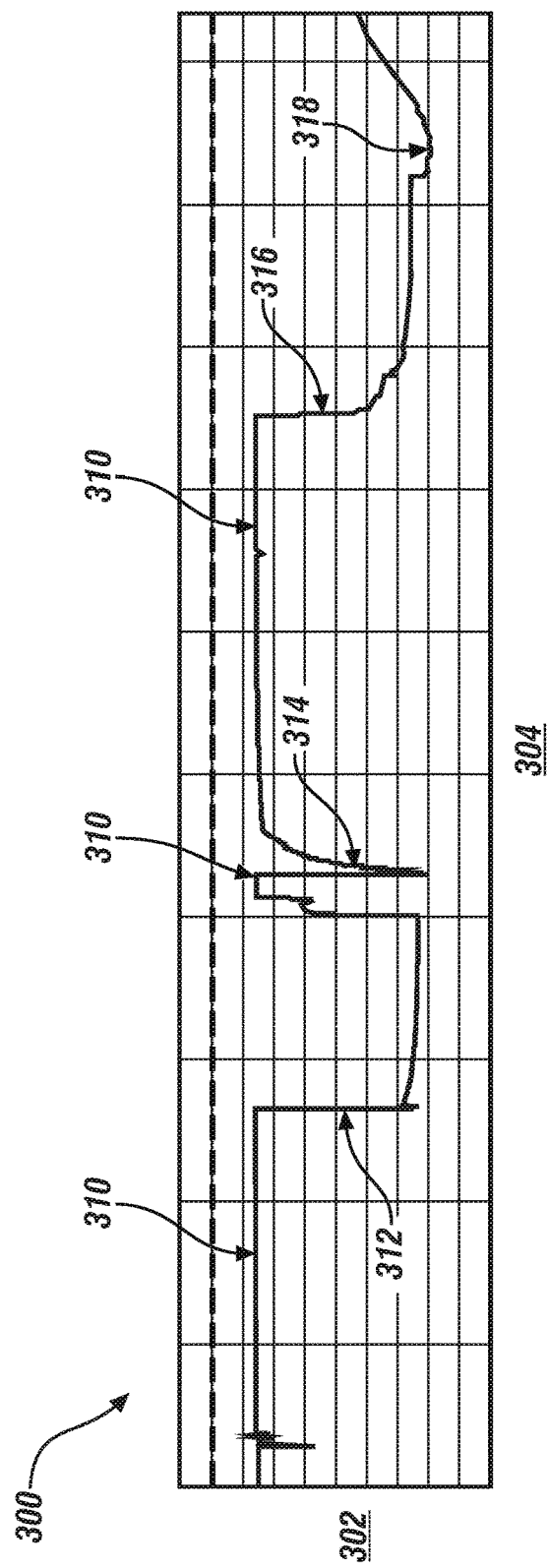
FIG. 3 graphically shows a plurality of signal waveforms that may be generated by an embodiment of the sensor including the resistive sensing element and associated signal conditioning circuit described with reference to FIG. 1, in accordance with the disclosure.

FIG. 3 graphically shows a plurality of signal waveforms that may be generated by the sensor 10, depending upon the presence or absence a fluid, wherein the fluid can include of water in liquid form, i.e., freestanding water, water in condensate form, i.e., moisture, or coolant. The graph 300 depicts magnitude of sensor signal waveform on the vertical axis 302, with time indicated on the horizontal axis 304. Portions of the signal waveform designated as 310 indicate the baseline sensor value. The portion of the signal waveform designated as 312 indicates signal output from the sensor 10 in the presence of freestanding water, and can be characterized as a negative step response, with a sustained drop in the voltage due to a reduced impedance across the sensor 10. The portion of the signal waveform designated as 314 indicates the signal output from the sensor 10 in the presence of coolant, and can be characterized as an initial negative step response followed by a rebound that is in the form of a positive decayed response. The portion of the signal waveform designated as 316 indicates the signal output from the sensor 10 in the presence of water spray or condensate, and can be characterized as a negative decayed response. The portion of the signal waveform designated as 318 indicates the signal output from the sensor 10 initially in the presence of water spray or condensate followed by exposure to coolant, and can be characterized as an initial negative step response followed by a rebound in the form of a positive decayed response.

Referring again to FIGS. 1 and 2, the sensor 10 and associated control routine 100 generates signal output 52 that indicates presence or absence of a fluid on the sensor 10, and further discriminates the signal output 52 to discern the substance of the fluid that is present at the sensor 10. This detection system discriminates between condensation, free standing water, and coolant in order to detect or prevent isolation loss which could lead to battery pack shut down or failure, and can permit the isolation of loss of battery pack as a result of too much water, moisture, and/or coolant. The sensor 10 and associated control routine 100 can be employed in any device that is susceptible to moisture, freestanding water, and/or coolant contamination.

When a voltage drop has been detected (126)(1), the signal waveforms including the voltage drop slopes are evaluated. This includes determining whether the signal output from the sensor 10 can be characterized as an initial negative step response followed by a rebound that is in the form of a positive decayed response (128), which is analogous to the portion of the waveform designated as element 314 in FIG. 3. If so (128)(1), the signal output from the sensor 10 indicates detection of the presence of coolant, water or another substance (130). This result, i.e., the presence of coolant, water or another substance is stored in memory and is communicated to an operator (132), including illuminating a dashboard lamp and/or communicating the result via a service tool or a telematics device. This result, i.e., presence of coolant, water or another substance can also be communicated to another controller, which can execute routines to mechanically and/or electrically isolate an electrical device that is proximal to the resistive sensing element 10.

If not (128)(0), the voltage drop slopes are evaluated to determine whether the signal waveform from the sensor 10 can be characterized as a negative step response with a sustained drop in the voltage (134), which is analogous to the portion of the waveform designated as element 312 in FIG. 3.

When the signal waveform from the sensor 10 can be characterized as a negative step response with a sustained drop in the voltage (134)(1), the signal output from the sensor 10 indicates detection of the presence of water (136), and monitoring continues with execution of steps 144, 146 and 148. If not (134)(0), the voltage level of the signal output from the sensor 10 is evaluated to determine if it is close to the initial value (138), and if so (138)(1), no voltage drop is detected (140), and monitoring continues with execution of steps 144, 146 and 148. When the voltage level of the signal output from the sensor 10 is close to the initial value (138)(0), a voltage drop is detected (142), and monitoring continues with execution of steps 144, 146 and 148.

In this manner, the control routine 100 can discriminate between presence of condensation, free standing water, and coolant at the sensor 10, and is thus able to detect presence of fluids near a proximal device such as an electrical device such as an inverter or high-voltage battery.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

What is claimed is:

1. A device for detecting presence of a fluid, comprising:
a resistive sensing element including a first conductive element proximal to a second conductive element, wherein the first conductive element is electrically isolated from the second conductive element;
a controller disposed to monitor electrical conductivity between the first conductive element and the second conductive element, the controller including an instruction set, the instruction set being executable to:
periodically monitor a signal associated with the electrical conductivity between the first conductive element and the second conductive element,
determine a signal waveform based upon the periodically monitored signal,
characterize the signal waveform,
detect presence of a fluid based upon the characterized signal waveform, including discriminating between a presence of condensation, free-standing water, and coolant based upon the characterized signal waveform,
electrically isolate an electrical device that is proximal to the resistive sensing element when either of free-standing water and coolant is detected, and
communicate the presence of the fluid.

2. The device of claim 1, wherein the instruction set is executable to detect presence of standing water at the resistive sensing element when the signal waveform is characterized as a step response.

3. The device of claim 1, wherein the instruction set is executable to detect presence of condensate water at the resistive sensing element when the signal waveform is characterized as a negative decayed response.

4. The device of claim 1, wherein the instruction set is executable to detect presence of coolant at the resistive sensing element when the signal waveform is characterized as an initial step response followed by a positive decayed response.

5. The device of claim 4, wherein the coolant comprises a solution including ethylene glycol, diethylene glycol, or propylene glycol.

6. A method for detecting presence of a fluid, comprising:
periodically monitoring a signal output from a resistive sensing element disposed in an environment, the resistive sensing element including a first conductive element proximal to and electrically isolated from a second conductive element, wherein the periodically monitored signal output corresponds to electrical conductivity between the first conductive element and the second conductive element;
determining a signal waveform based upon the periodically monitored signal output;
characterizing the signal waveform;
detecting presence of a fluid based upon the characterized signal waveform, including discriminating between a presence of condensation, free-standing water, and coolant based upon the characterized signal waveform;
electrically isolating an electrical device that is proximal to the resistive sensing element when either of free-standing water and coolant is detected; and
communicating the presence of the fluid.

7. The method of claim 6, further comprising detecting presence of standing water at the resistive sensing element when the signal waveform is characterized as a step response.

8. The method of claim 6, further comprising detecting presence of condensate water at the resistive sensing element when the signal waveform is characterized as a negative decayed response.

9. The method of claim 6, further comprising detecting presence of coolant at the resistive sensing element when the signal waveform is characterized as an initial step response followed by a positive decayed response.

10. The method of claim 9, wherein the coolant comprises a solution including ethylene glycol, diethylene glycol, or propylene glycol.

11. A device for detecting presence of a fluid, comprising:
a sensing element disposed on a substrate, the sensing element including a first conductive element including a plurality of first leg portions and a second conductive element including a plurality of second leg portions, wherein the first leg portions alternate with the second leg portions and wherein the first conductive element is electrically isolated from the second conductive element;
a controller disposed to monitor electrical conductivity between the first conductive element and the second conductive element, the controller including an instruction set, the instruction set being executable to:
determine a baseline state for the sensing element; and then periodically determine a signal output from the sensing element,
determine a signal waveform based upon the periodically determined signal output from the sensing element;
compare the signal waveform and the baseline state for the electrical conductivity,
detect presence of a fluid based upon the signal waveform compared to the baseline state for the electrical conductivity, including discriminating between a presence of condensation, free-standing water, and coolant based upon the signal waveform,
electrically isolate an electrical device that is proximal to the resistive sensing element when either of free-standing water and coolant is detected, and
communicate the presence of the fluid.

12. The device of claim 11, wherein the instruction set is executable to detect presence of standing water at the resistive sensing element when the signal waveform is characterized as a step response.

13. The device of claim 11, wherein the instruction set is executable to detect presence of condensate water at the resistive sensing element when the signal waveform is characterized as a negative decayed response.

14. The device of claim 11, wherein the instruction set is executable to detect presence of coolant at the resistive sensing element when the signal waveform is characterized as an initial step response followed by a positive decayed response.

15. The device of claim 14, wherein the coolant comprises a solution including ethylene glycol, diethylene glycol, or propylene glycol.

* * * * *